United States Patent
Collin-Djangone et al.

(10) Patent No.: US 9,095,630 B2
(45) Date of Patent: *Aug. 4, 2015

(54) VECTORIZATION OF DSRNA BY CATIONIC PARTICLES AND USE OF SAME ON A SKIN MODEL

(75) Inventors: Christine Collin-Djangone, Amblainville (FR); Jean-Thierry Simonnet, Cachan (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/436,775

(22) Filed: May 19, 2006

(65) Prior Publication Data

US 2007/0003501 A1    Jan. 4, 2007

Related U.S. Application Data

(60) Provisional application No. 60/689,528, filed on Jun. 13, 2005.

(30) Foreign Application Priority Data

May 19, 2005 (FR) ..................................... 05 51304

(51) Int. Cl.
| | |
|---|---|
| *A61K 48/00* | (2006.01) |
| *A61K 47/48* | (2006.01) |
| *A61K 31/713* | (2006.01) |
| *B82Y 5/00* | (2011.01) |
| *C12N 15/113* | (2010.01) |

(52) U.S. Cl.
CPC ............. *A61K 47/488* (2013.01); *A61K 31/713* (2013.01); *A61K 47/48815* (2013.01); *B82Y 5/00* (2013.01); *C12N 15/113* (2013.01)

(58) Field of Classification Search
CPC ............................ A61K 47/488; C12N 15/113
See application file for complete search history.

(56) References Cited

U.S. PATENT DOCUMENTS

| | | | |
|---|---|---|---|
| 6,482,804 B1 * | 11/2002 | Musunuri et al. | 514/44 A |
| 2005/0222071 A1 | 10/2005 | Duranton et al. | |
| 2005/0238606 A1 * | 10/2005 | Dokka et al. | 424/70.13 |
| 2006/0134221 A1 * | 6/2006 | Geall | 424/489 |

FOREIGN PATENT DOCUMENTS

| | | |
|---|---|---|
| JP | 2005-13224 | 1/2005 |
| WO | WO 2005/007196 | 1/2005 |

OTHER PUBLICATIONS

Smith et al, Phys. Chem. Chem. Phys. 2:1305-1310, 2000.*
Greenwood et al., Journal of the European Ceramic Society, 1999, 19:479-488.*

(Continued)

*Primary Examiner* — Jon E Angell
(74) *Attorney, Agent, or Firm* — Oblon, McClelland, Maier & Neustadt, L.L.P.

(57) ABSTRACT

The present invention relates to vectorization of double stranded RNA oligonucleotides by cationic particles chosen from among surfactant micelles, block or non-block polymer micelles, cationic liposomes and niosomes, cationic oleosomes and cationic nanoemulsions, as well as from among cationic organic or inorganic particles and nanocapsules, and to the use of compositions comprising the association of at least one dsRNA and at least one cationic particle on skin models.

20 Claims, 5 Drawing Sheets

Block-It Fluorescent Oligo (DAPI)

Block-It Fluorescent Oligo + Lipofectamine 2000 (DAPI)

(56) References Cited

OTHER PUBLICATIONS

Kaspar, R., et al, "Reporter Gene Delivery and Potent Inhibition Expression by Modified and Unmodified siRNAs in a Mouse Skin Model," Journal of Investigate Dermatology, Apr. 2005, vol. 124, No. 4, Suppl. S. pp. A81. XP008062688.

Yano Junichi et al., "Antitumor Activity of Small Interfering RNA/ Cationic Liposome Complex in Mouse Models of Cancer," Clinical Cancer Research: An Official Journal of the American Association for Cancer Research, Nov. 15, 2004, vol. 10, No. 22, XP002375948.

Sebastien Spagnov, et al., "Differences in the Formulation, Cellular Uptake, and Delivery with Plasmid DNA," Biochemistry 2004, 43, 13348-13356. XP-002375949.

Zheng Ma, et al., "Cationic Lipids Enhance siRNA-mediated Interferon Response in Mice," Biochemical and Biophysical Research Communications, May 13, 2005, pp. 755-759. XP-002375750.

Georg Mellitzer, et al., "Spatial and Temporal 'knock down' of Gene Expression by Electroporation of Double-Stranded RNA and Morpholinos into Early Postimplantation Mouse Embryos," Mechanisms of Development, 118, (2002), XP-0023795950.

Schmook et al., "Comparison of Human Skin or Epidemis Models with Human and Animal Skin in In-Vitro Percutaneous Absorption," International Journl of Pharmaceutics, Mar. 14, 2001, Netherlands, vol. 215, No. 1-2, pp. 51-56. XP002390502.

Office Action issued Jul. 30 2013 in Japanese Application No. 2006-139474 (English Translation).

Office Action issued Sep. 13, 2011 in Japanese Patent Application No. 2006-139474 (submitting English-language translation).

English translation of Kaori Matsumoto, et al., "A Role of the Drug Delivery Carriers in Material Permeation by a Three-dimensional Cultured Human Skin Model", Journal of Pharmaceutical Science and Technology, vol. 62, Mar. 5, 2002, 3 pages.

English translation of Tomohiro Hikima, et al., "Skin Model for Studies of Percutaneous Treatment System Research", Drug Delivery System, vol. 16, No. 3, May 10, 2001, 9 pages.

English translation of Toshio Kojima, et al., Utilization of a Kit in Human Three-Dimensional Dermal Model "Neoderm-ED" for Alternative to Skin Irritation Testing:, Proceedings of the Japanese Environmental Mutagen Society, vol. 33, Nov. 30, 2004, 4 pages.

* cited by examiner

Block-It Fluorescent Oligo (DAPI)

Block-It Fluorescent Oligo + Lipofectamine 2000 (DAPI)

Block-It Fluorescent Oligo + E2 (x40, DAPI)

E2 (x40, DAPI)

Block-It Fluorescent Oligo + E2
(x100, DAPI)

Block-It Fluorescent Oligo + E2
(x100)

Block-It Fluorescent Oligo (x40, DAPI)

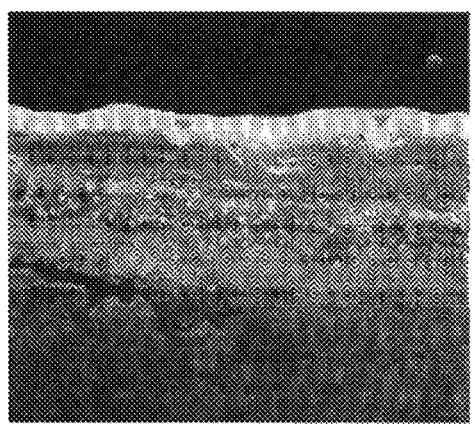 
Block-It Fluorescent Oligo + E2
(x40, DAPI)
Fig. 2B
Block-It Fluorescent Oligo + E2
(x40)
Fig. 2C

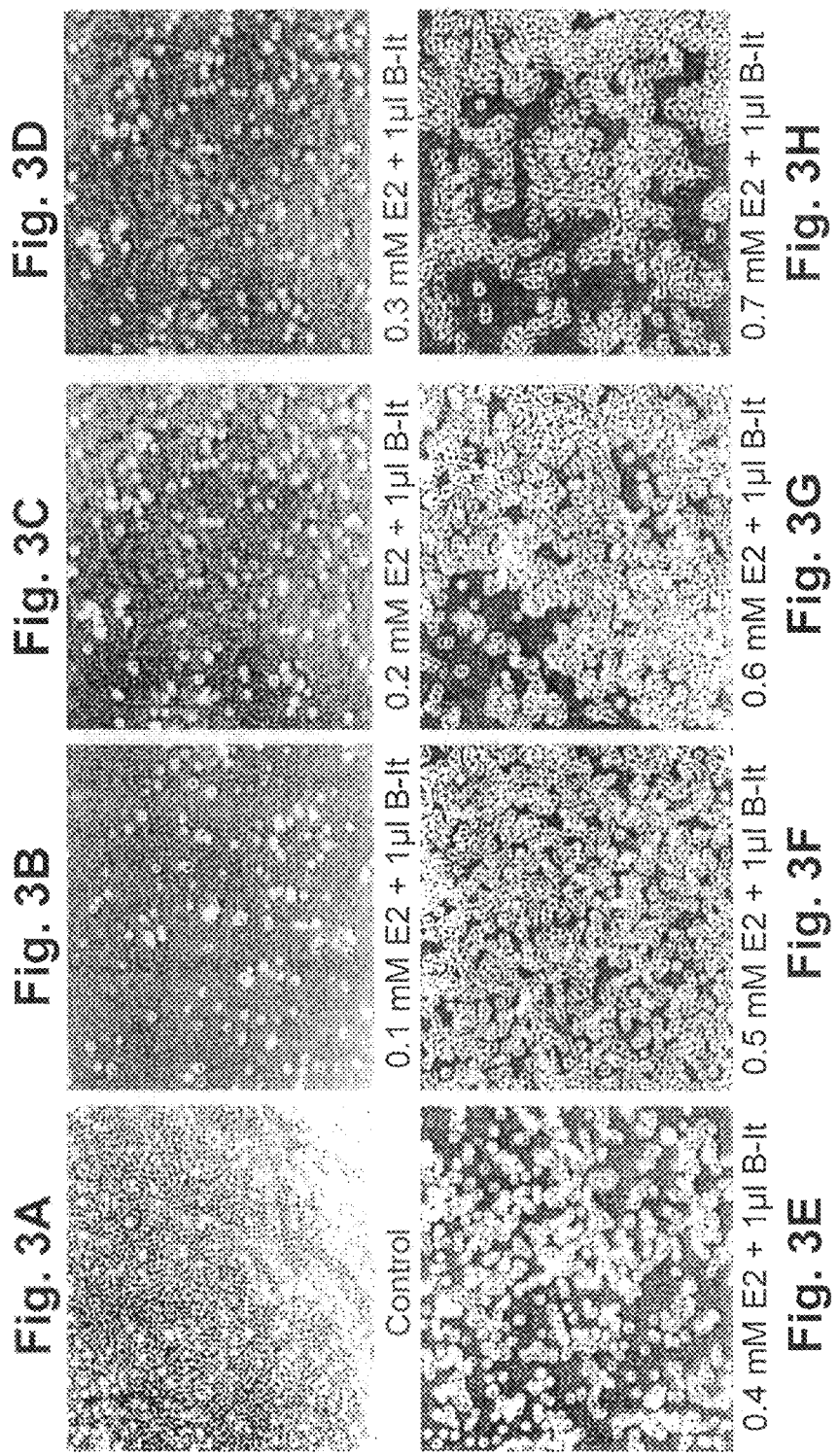

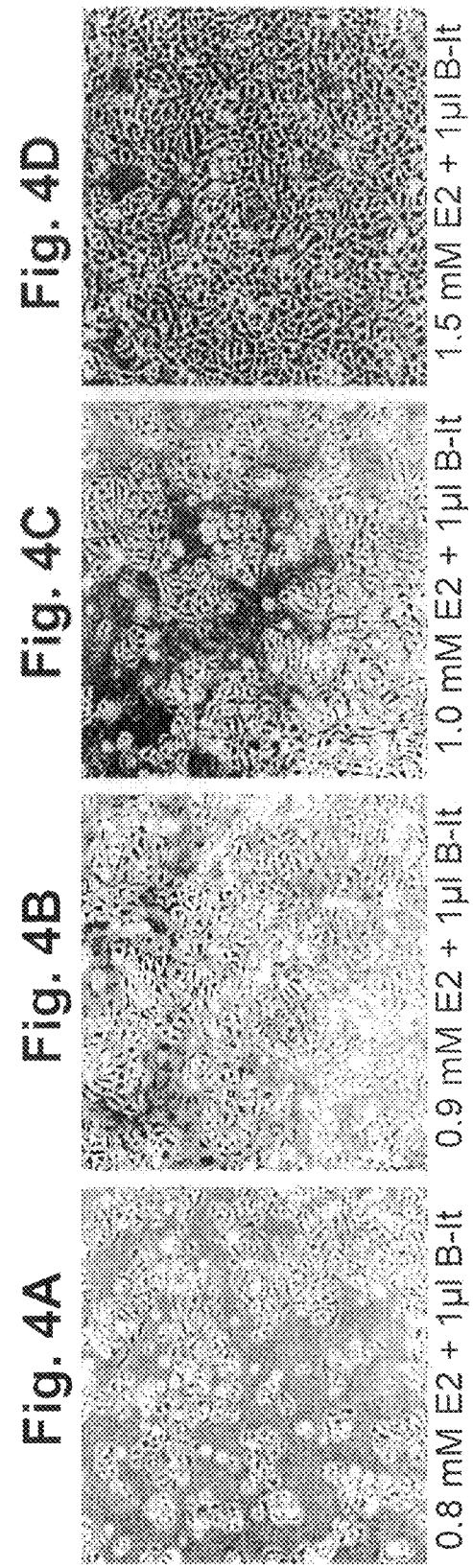

VECTORIZATION OF DSRNA BY CATIONIC PARTICLES AND USE OF SAME ON A SKIN MODEL

REFERENCE TO PRIOR APPLICATIONS

This application claims priority to U.S. provisional application 60/689,528 filed Jun. 13, 2005, and to French patent application 0551304 filed May 19, 2005, both incorporated herein by reference.

FIELD OF THE INVENTION

The present invention relates to vectorization of double stranded RNA oligonucleotides by cationic particles chosen from among surfactant micelles, block or non-block polymer micelles, cationic liposomes and niosomes, cationic oleosomes and cationic nanoemulsions, as well as from among cationic organic or inorganic particles and nanocapsules, and to the use of compositions comprising the association of at least one dsRNA and at least one cationic particle on skin models.

BACKGROUND OF THE INVENTION

Research is being conducted on the use of substances having specific activity, such as specific biological activity, in the cosmetics field such as skin care or hair care, but also in the dermatological and pharmaceutical fields.

Recently, the use of dsRNA and more particularly siRNA (containing 12 to 40 nucleotides) has made it possible to achieve specific activity in inhibition of the synthesis of a target protein. The molecular mechanism taking place involves double stranded RNA fragments composed of 12 to 40 nucleotides. Degradation of the target mRNA is achieved by activation of the complex known as RISC(RNA Induced Silencing Complex), which acts by fixation of the anti-sense strand of the dsRNA onto the mRNA. These double stranded RNA oligonucleotides are also known as dsRNA or else siRNA (for "short interfering" RNA); see Tuschl T., Chem. Biochem. 2001, 2, 239-245; Nykanen A et al., Cell 2001, 107, 309-321, Dorsett Y., Nature, April 2004, Vol. 3, pages 318-329; and Downward, J., BMJ 2004, 328, 1245-1248.

However, the topical application, on skin, mucous membranes or skin models, of these siRNA, which can have molecular weights of approximately 15 to 17 kD, gives rise to the problem of penetration. In fact, for the specific activity relative to the selected siRNA to be effective, it must penetrate into the target cell (such as the keratinocytes or the melanocytes, etc.) as far as the cytoplasm. The stratum corneum, the site of the skin barrier function, is difficult to penetrate.

International Application WO 03/101376 describes cosmetic preparations comprising at least one double stranded RNA oligonucleotide. In this publication, the oligonucleotide is necessarily complexed with a cationic polymer such as PEI or chitosan, after which this complex of oligonucleotide and cationic polymer can be encapsulated in liposomes or niosomes and/or adsorbed at the surface of particles such as liposomes, niosomes, oleosomes, nanospheres and nanocapsules. Therefore, the dsRNA is necessarily complexed with a cationic polymer before being associated with a type of particle. In addition, the surfactant micelles are not described as an efficient medicinal solution for vectorization of siRNA.

In the article "Intercellular adhesion molecule-1 suppression in skin by topical delivery of anti-sense oligonucleotides," Mehta et al. (J. Invest. Dermatol. 115, 805-812, 2000), the authors transport single stranded RNA in an emulsion containing 25% of surfactants (10% of glyceryl stearate and 15% of 400E stearate). Besides the fact that this article does not describe the siRNA, the proposed medicinal solution is not compatible with good tolerance. In fact, the 25% of surfactants will have the effect of destroying the barrier function of the skin, thus increasing its permeability to external elements and dramatically favoring its dehydration: results that are not sought in the fields of application envisioned by the present invention.

In the publication "Lipidic carriers of siRNA: differences in the formulation, cell uptake and delivery with plasmid DNA," Spagnou et al. (Biochemistry, 43, 13348-56, 2004), the authors use cationic liposomes such as lipofectamine 2000 or DOPE liposomes "cationized" with cholesteryloxy-carbonyl-3,7-diazanone-1,9-diamine (CDAN). For safety reasons, lipofectamine cannot be used on human skin.

Other publications (Yano Junichi et al., Clinical Cancer Research, 2004, Spagnou et al., Biochemistry, 2004, and Ma Zheng et al., Biochemical and Biophysical Research Communications, 2004) have proposed associating siRNA with cationic vesicles composed of oleyl chain lipids containing unsaturated bonds that make them very sensitive to oxidation, and phospholipids, these vesicles being intended to be used immediately after preparation, because they are not very stable in time.

International Patent Application WO 2004/046354 describes the use of siRNA for cutaneous dysfunction, preferably at the dermis level. The compositions described, such as PIT and W/O, O/W and W/O/W emulsions, are all non-ionic. In that patent application, no appraisal is made of the major and essential interest of using cationic surfactants in cationic particles in order to favor penetration of the siRNA into cutaneous structures. Moreover, although the PIT can be smaller than μm size, they are necessarily nonionic, as described in International Patent WO96/28132.

International Application WO 03/106636 describes the association of a polynucleotide with a cationic surfactant such as cetyltriammonium chloride to form a complex. It is then necessary to stabilize this complex by an incubation step at a temperature of between 35 and 50° C. In a second step, it is possible to dehydrate the mixture to obtain therefrom a powder, which will then be diluted in a chosen solvent before use (injection). Once the complex has been formed, it is also possible to stabilize it by addition of an amphiphilic lipid, which can be a nonionic surfactant. This ternary association is then dehydrated to obtain a powder, which will then be diluted in an appropriate aqueous solution.

International Application WO 03/106636 does not specify that the concentration of the cationic surfactant must be above the CMC (critical micellar concentration) in order to form the complex of polynucleotide and cationic surfactant, since the complex can be formed below the CMC. It is only once this complex has been formed that the addition of another amphiphilic compound capable of forming micelles is envisioned. In this way the integration of a complex of polynucleotide and cationic surfactant into amphiphilic micelles is achieved. Thus the question of associating cationic particles with a polynucleotide is not addressed in that document.

However, there remains a need to identify a way to permit the penetration of siRNA into the skin models.

SUMMARY OF THE INVENTION

Accordingly, one object of the present invention is to provide compositions, kits, and methods for permitting the penetration of double stranded and/or siRNA into skin and skin models.

The invention provides a composition comprising at least one dsRNA associated with at least one cationic particle of a size less than or equal to 1 μm and having a zeta potential of from 10 to 80 mV, and which is chosen from a surfactant micelle, a block polymer micelle, a liposome of nonionic and/or cationic surfactants, niosomes, oleosomes, particles of nanoemulsions, nanocapsules, organic particles, or inorganic particles.

The invention also provides kits containing such compositions with a skin model.

The invention also provides methods of using the compositions and kits for inhibiting protein expression in the cells of the skin and/or skin model.

The invention also provides methods of preparing a skin model by applying the compositions to a skin model.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A shows Block-It Fluorescent Oligo (DAPI); FIG. 1B shows Block-It Fluorescent Oligo+Lipofectamine 2000 (DAPI); FIG. 1C shows Block-It Fluorescent Oligo+E2 (×40, DAPI); FIG. 1D: E2 (×40, DAPI); FIG. 1E shows Block-It Fluorescent Oligo+E2 (×100, DAPI); and FIG. 1F shows Block-It Fluorescent Oligo+E2 (×100).

FIGS. 2A-2C show the results of Cell targeting in Episkin—day 13 where FIG. 2A shows Block-It Fluorescent Oligo (×40, DAPI); and FIGS. 3A-3H and FIGS. 4A-4D show visualization of the effect of the formulation comprising octyl glucoside and CTAB in different concentrations on the viability of HaCaT cells.

DETAILED DESCRIPTION OF THE INVENTION

Figure 1A:
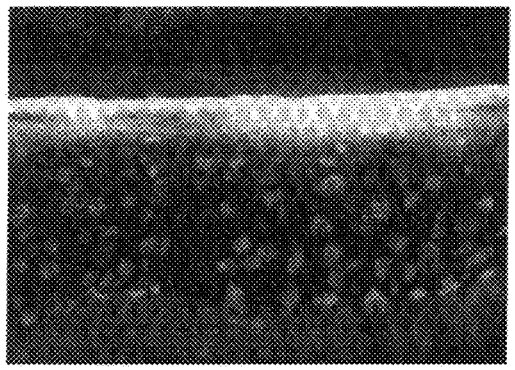
FIGS. 1A-1F show the results of cell targeting in Episkin—day 6 where

Unexpectedly, the association of siRNA with cationic particles permits a very significant improvement for penetrating into target cells of a tissue such as the skin, especially skin models. After penetration, the siRNA becomes active. The penetration can be evaluated using a fluorescent marker fixed on the siRNA, and its activity can be evaluated by quantification of the targeted messenger by quantitative PCR or by assay of the protein corresponding to the targeted messenger RNA. The cationic particles of the invention can be surfactant micelles, block or non-block polymer micelles, cationic liposomes and niosomes, cationic oleosomes, cationic nanoemulsions, as well as cationic organic or inorganic particles and nanocapsules.

The present invention relates to the association of cationic particles with at least one dsRNA that will adhere to the surface of the particle, the latter acting as a vehicle to allow it to penetrate into the cutaneous structures and into the target cells of the skin, especially skin models.

Thus a first object of the invention relates to a kit comprising a skin model and to a composition comprising at least one double stranded RNA oligonucleotide associated with at least one cationic particle of size less than or equal to 1 μm, of zeta potential between 10 and 80 mV, chosen from among surfactant micelles, preferably micelles of nonionic amphiphilic surfactants and cationic surfactants, block polymer micelles, preferably micelles of cationic amphiphilic block polymer, micelles of nonionic amphiphilic block polymer and of cationic amphiphilic block polymer and micelles of nonionic amphiphilic block polymer and of cationic surfactant, liposomes of nonionic and cationic surfactants, niosomes, oleosomes, particles of nanoemulsions, nanocapsules, organic particles or inorganic particles.

The cationic particles according to the invention are particles having a size less than or equal to 1 μm, preferably less than or equal to 500 nm, even more preferentially less than or equal to 300 nm, which can be measured with, for example, a laser granulometer of the type BI90 plus of the Brookhaven Co., and which have a zeta potential of between 10 and 80 mV, measurable with a zetameter of the type DELSA 440 of the Coultronics Co.

Hereinafter there is presented a non-exhaustive list of cationic particles than can be used according to the invention.

Surfactant Micelles

As known in the art, micelles are aggregates that amphiphilic molecules form spontaneously when they are solubilized in water or oil above a certain critical concentration: the CMC.

The micelles that can be used within the scope of the invention are composed of at least one cationic surfactant. This cationic surfactant can be associated with one or more nonionic amphiphilic surfactants.

The person skilled in the art will advantageously select the nonionic and cationic surfactants in the 1998 and subsequent editions of McCutcheon's "Emulsifiers and Detergents".

Non-limiting examples of the cationic surfactants that can be used within the scope of the invention are listed hereinafter.

Non-limiting examples of nonionic surfactants that can be used are: alkyl and polyalkyl (C6 to C30, saturated or unsaturated, branched or linear) esters or ethers of POE, glycerol and polyglycerol, of sorbitan with or without oxyethylene groups, of sucrose, of glucose with or without oxyethylene groups, of maltose and of POP-POE. If mixtures of nonionic surfactants and cationic surfactants are included, their respective proportions by weight will be between 99/1 and 1/99.

The proportions of surfactants forming the micelles will be dependent on the CMC thereof. Within the scope of the invention, however, the concentration of micellar surfactants will be between 0.1 and 10% and preferably between 0.2 and 5% by weight relative to the total weight of the composition.

Block Polymer Micelles

The micelles of amphiphilic block polymers can be prepared by the method described in International Application WO 04/035013.

The block copolymers that are useful for preparation of micelles associated with the dsRNA according to the invention are, in particular, amphiphilic block polymers, preferably of nonionic, di-block or tri-block type that can form micelles upon contact with water. In particular, they are of the di-block type (A-B) or of the tri-block type (A-B-A), where A corresponds to a nonionic hydrophilic polymeric block and B to a hydrophobic polymeric block. The molecular weight of the polymers can be between 1000 and 100,000, and the A/B ratio can be between 1/100 and 50/1.

The nonionic hydrophilic polymeric block can be chosen from among ethylene polyoxide (POE), polyvinylpyrrolidone (PVP) and polyacrylic acid (PAA).

The hydrophobic polymeric block can be chosen from among polystyrene, poly(tert-butylstyrene), poly(methyl methacrylate), poly(ethyl acrylate), poly(butyl acrylate), poly(butyl methacrylate), poly(vinyl acetate), polycaprolactones, polycaprolactams, polydimethylsiloxanes, polyoxides of C3 to C6 alkylene, poly(aspartic acid), poly(lactic acid), poly(glycolic acid), polyleucine, polybutadienes, polyethylenes, polypropylenes and polybutylenes.

The block copolymer is preferably chosen from among the following block copolymers:
  propylene polyoxide/ethylene polyoxide
  polystyrene/polyoxyethylene
  polymethyl methacrylate/polyoxyethylene
  polybutyl methacrylate/polyoxyethylene
  polyoxybutylene/polyoxyethylene
  polycaprolactone/polyoxyethylene
  polyethylene/polyoxyethylene
  polyoxyethylene/polyoxybutylene/polyoxyethylene.

Within the scope of the invention, the following can be added to add to the micellar composition:
  a cationic amphiphilic block polymer in which one of the blocks is cationic and can be chosen from among, for example:
    trimethylethylammonium polymethacrylate;
    quaternized dimethylaminoethyl polymethacrylate;
    polymethylvinylimidazolium;
    polyvinylbenzyltrimethylammonium chloride;
  the association of a nonionic amphiphilic block polymer with a cationic amphiphilic block polymer is such that the ratio between the two will be between 99/1 and 1/99; and/or
  at least one cationic surfactant such as listed hereinafter.

In this case, the respective ratio between the nonionic amphiphilic block polymer and the cationic surfactant will be between 50/50 and 99/1.

Within the scope of the invention, the concentration of micellar block polymers that are or are not associated with a cationic surfactant will be between 0.1 and 10% and preferably between 0.2 and 5% by weight relative to the total weight of the composition.

In an alternative version of the invention, it is also possible to form micelles composed of cationic amphiphilic block polymers such as described in the foregoing.

Liposomes and Niosomes

The nonionic amphiphilic lipids capable of forming nonionic liposomes are in particular those described in Patent Application EP 0582503.

In particular, the nonionic amphiphilic lipids can be composed of a mixture of esters of at least one polyol chosen in the group formed by polyethylene glycol having 1 to 60 ethylene oxide units, sorbitan, sorbitan with 2 to 60 ethylene oxide units, glycerol with 2 to 30 ethylene oxide units, polyglycerols with 2 to 15 glycerol units, sucroses, glucoses with 2 to 30 ethylene oxide units, and at least one fatty acid having a C5 to C17 saturated or unsaturated, linear or branched alkyl chain, the number of alkyl chains per polyol group being between 1 and 10.

The expression "mixture of esters" covers not only mixtures of pure esters of different chemical families but also products that contains a plurality of chemically pure polyol esters of the same family in variable proportions. This is the case in particular of products that have a statistical formula in their hydrophilic part, such as a polyglycerol ester of formula $CO—(OCH_2—CHOH—CH_2)_n—OH$, where n is a statistical value, and that can contain diverse proportions of esters for which n=1, n=2, n=3, n=4, etc.; this is also the case of esters containing a plurality of alkyl chains in their lipophilic part, such as the cocoates, which contain C5 to C17 alkyl chains, or the isostearates, where the C17 alkyl chains are a complex mixture of isomeric forms; it is also the case of products composed of mixtures of mono-, di-, tri- or polyesters of one and the same polyol. It must be noted that a product that would contain only a single ester capable of forming vesicles together with impurities of another type could not be used according to the invention.

Commercial esters that can be used alone according to the invention, because in reality they are mixtures of esters are, for example, the following:
  the partial esters of sorbitan (or sorbitol anhydride) and fatty acid, sold under the trade names "SPAN 20, 40, 60 and 80" by the ICI Co.;
  sorbitan isostearate, sold under the trade name "SI 10 R NIKKOL" by the NIKKO Co.;
  sorbitan stearate with 4 ethylene oxide units, sold under the name "TWEEN 61" by the ICI Co.;
  polyethylene glycol stearate with 8 ethylene oxide units, sold under the name "MYR J 45" by the ICI Co.;
  polyethylene glycol monostearate of formula EMI6.1, in which formula n is equal to 4, sold under the name "MYS 4" by the NIKKO Co.;
  polyethylene glycol stearate of molecular weight 400, chemical grade or grade produced by biotechnology, sold by the UNICHEMA Co.;
  diglyceryl stearate with 4 ethylene oxide units, sold under the name "HOSTACERINE DGS" by the HOECHST Co.;
  tetraglycerol stearate, sold under the name "TETRAGLYN 1S" by the NIKKO Co.;
  diglyceryl isostearate, sold by the SOLVAY Co.;
  diglyceryl distearate, sold under the name "EMALEX DSG 2" by the NIHON Co.;
  sucrose mono-, di- and tripalmitostearates, sold under the names "F50, F70, F110 AND F160 CRODESTA" by the CRODA Co.;
  the mixture of sucrose mono- and dipalmitostearates, sold under the name "GRILLOTEN PSE 141 G" by the GRILLO Co.;
  the mixture of sucrose stearate and sucrose cocoate, sold under the name "ARLATONE 2121" by the ICI Co.;
  methylglucose distearate with 20 ethylene oxide units, sold under the name 'GLUCAM E 20 DISTEARATE" by the AMERCHOL Co.

Of course, it is possible to use mixed combinations of these different products that are already mixtures or mixed combinations of these products with pure products.

The cationic surfactants are chosen in the list hereinafter, in such a way that they impart a pH of between 5 and 8 to the dispersion, wherein the ratio by weight between the quantity of nonionic amphiphilic lipids and the quantity of cationic surfactants in the lipid phase is between 50/1 and 50/25, and the ratio by weight between the lipid phase and the aqueous dispersion phase is between 1/1,000 and 300/1,000.

Oleosomes

The oleosomes relating to the invention are described in Patent Application EP 0705593. They comprise an emulsion of the oil-in-water type formed from oil globules provided with a lamellar liquid crystal coating and dispersed in an aqueous phase, characterized in that each oil globule is individually coated with a monolamellar or oligolamellar layer (1 to 10 lamellas that are visible under the transmission electron microscope after cryofracture) obtained from at least one lipophilic surface-active agent, at least one hydrophilic surface-active agent and at least one cationic surfactant, which imparts a pH ranging from 5 to 8 to the emulsion, the coated oil globules having an average diameter less than 500 nanometers.

The lipophilic surface-active agent and the hydrophilic surface-active agent each contain at least one saturated fatty chain having more than approximately 12 carbon atoms. More preferentially, this fatty chain contains 16 to 22 carbon atoms.

According to another preferential embodiment of the invention, the lipophilic surface-active agent has an HLB of between approximately 2 and approximately 5. As is well known, there is understood by HLB (hydrophilic-lipophilic balance) the equilibrium between the dimension and strength of the hydrophilic group and the dimension and strength of the lipophilic group of the surface-active agent.

Examples of such lipophilic surface-active agents are sucrose distearate, diglyceryl distearate, tetraglyceryl tristearate, decaglyceryl decastearate, diglyceryl monostearate, hexaglyceryl tristearate, decaglyceryl pentastearate, sorbitan monostearate, sorbitan tristearate, diethylene glycol monostearate, the glycerol ester of palmitic and stearic acids, 2 OE polyoxyethylene monostearate (containing 2 oxyethylene units), glyceryl mono- and dibehenate, and pentaerythritol tetrastearate.

The hydrophilic surface-active agent preferably has an HLB of between approximately 8 and approximately 12.

As examples of such hydrophilic surface-active agents there can be cited the following compounds: polyoxyethylene (4 OE) sorbitan monostearate, polyoxyethylene (20 OE) sorbitan tristearate, polyoxyethylene (8 OE) monostearate, hexaglyceryl monostearate, polyoxyethylene (10 OE) monostearate, polyoxyethylene (12 OE) distearate and polyoxyethylene (20 OE) methylglucose distearate.

The cationic surfactants can be chosen from among the compounds cited hereinafter.

Nanoemulsions

The cationic particles can also be chosen from among the oil-in-water nanoemulsions containing an oily phase dispersed in an aqueous phase, wherein the oil globules have a number-average size less than 100 nm, characterized in that they comprise at least one amphiphilic lipid comprising at least one nonionic amphiphilic lipid and one cationic amphiphilic lipid, the oily phase and the amphiphilic lipids being present in a content such that the weight ratio of the oily phase to amphiphilic lipid ranges from 3 to 10.

The nanoemulsions generally have a bluish transparent appearance. Their transparency is measured by the coefficient of transmittance at 600 nm—ranging from 10 to 90%—or else by turbidity. The turbidity of the compositions of the invention ranges from 60 to 400 NTU and preferably from 70 to 300 NTU, which turbidity is measured with the portable HACH turbidimeter, model 2100 P, at approximately 25° C.

The oil globules of the nanoemulsions of the invention have a number-average size of less than 100 nm, preferably ranging from 20 to 80 nm and more preferentially from 40 to 60 nm. Reduction of the size of the globules makes it possible to favor penetration of the active agents into the superficial layers of the skin (vehicle effect).

The nanoemulsions according to the invention are preferably prepared at temperatures ranging from 4 to 45° C., and so they are compatible with heat-sensitive active agents.

These dispersions are described in the following Applications in particular: EP 0728460, EP 0879589, EP 1010413, EP 1010414, EP 1010416, EP 1013338, EP 1016453, EP 1018363, EP 1025898 and EP 1120102. In all of these applications, it is specified that an ionic surfactant will be added to the nonionic surfactant (or mixture) in order to improve the stability of the particles.

In the case of the present application, exclusively one or more cationic surfactants will be used as the ionic surfactant.

The proportions indicated in the foregoing references are to be adopted and, as an example of cationic surfactants, the list common to all of the particles will be used.

The nonionic surfactants, preferably soluble or dispersible in water, contain at least one hydrophobic sequence and at least one hydrophilic sequence.

The nonionic amphiphilic lipids of the invention are preferably chosen from among;
1/siliconized surfactants,
2/amphiphilic lipids that are liquid at temperatures lower than or equal to 45° C., chosen from among the esters of at least one polyol and at least one fatty acid containing at least one saturated or unsaturated, linear or branched and especially unsaturated or branched $C_8$ to $C_{22}$ alkyl chain, the polyol being chosen in the group formed by polyethylene glycol containing 1 to 60 ethylene oxide units, sorbitan, glycerol, which can contain from 2 to 30 ethylene oxide units, and the polyglycerols containing from 2 to 15 glycerol units.
3/esters of fatty acid and sugar and ethers of fatty alcohol and sugar,
4/surfactants that are solid at a temperature equal to 45° C., chosen from among the fatty esters of glycerol, the fatty esters of sorbitan and the fatty esters of oxyethylene sorbitan, the ethoxylated fatty ethers and the ethoxylated fatty esters,
5/block copolymers of ethylene oxide (A) and propylene oxide (B), and mixtures of these surfactants.

1/The siliconized surfactants that can be used according to the invention are siliconized compounds containing at least one oxyethylene chain $—OCH_2CH_2—$ and/or oxypropylene chain $—OCH_2CH_2CH_2—$. There can be cited those described in U.S. Pat. Nos. 5,364,633 and 5,411,744.

The siliconized surfactant used according to the present invention is preferably a compound of formula (II):

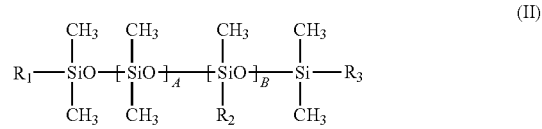

in which:
$R_1$, $R_2$, $R_3$, each independently of the others, represents a $C_1$ to $C_6$ alkyl radical or a $—(CH_2)_x—(OCH_2CH_2)_y—(OCH_2CH_2CH_2)_n—OR_4$ radical, wherein at least one radical $R_1$, $R_2$ or $R_3$ is not an alkyl radical; $R_4$ being a hydrogen atom, an alkyl radical or an acyl radical; A is an integral number ranging from 0 to 200;
B is an integral number ranging from 0 to 50; with the proviso that A and B are not equal to zero at the same time;
x is an integral number ranging from 1 to 6;
y is an integral number ranging from 1 to 30;
z is an integral number ranging from 1 to 5.

According to a preferred embodiment of the invention, in the compound of formula (X), the alkyl radical is a methyl radical, x is an integral number ranging from 2 to 6 and y is an integral number ranging from 4 to 30.

As an example of siliconized surfactants of formula (II), there can be cited the compounds of formula (III):

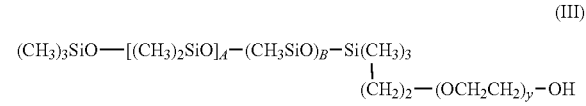

in which A is an integral number ranging from 20 to 105, B is an integral number ranging from 2 to 10 and y is an integral number ranging from 10 to 20.

As an example of siliconized surfactants of formula (II), there can also be cited the compounds of formula (IV):

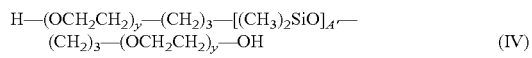
(IV)

in which A' and y are integral numbers ranging from 10 to 20.

As siliconized surfactants there can be used in particular those sold by the Dow Corning Co. under the names DC 5329, DC 7439-146, DC2-5695 and Q4-3667. The compounds DC 5329, DC 7439-146, and DC2-5695 are compounds of formula (XI), in which, respectively, A is 22, B is 2 and y is 12; A is 103, B is 10 and y is 12; A is 27, B is 3 and y is 12.

The compound Q4-3667 is a compound of formula (IV), in which A is 15 and y is 13.

2/The amphiphilic lipids that are liquid at temperatures lower than or equal to 45° C. can be chosen in particular from among:

polyethylene glycol isostearate of molecular weight 400 (CTFA name: PEG-8 isostearate), sold under the name Prisorine 3644 by the UNICHEMA Co.;

diglyceryl isostearate, sold by the SOLVAY Co.;

polyglycerol laurate containing 2 glycerol units (polyglyceryl-2 laurate), sold under the name Diglycerin monolaurate by the SOLVAY Co.;

sorbitan oleate, sold under the name SPAN 80 by the ICI Co.;

sorbitan isostearate, sold under the name NIKKOL SI 10R by the NIKKO Co.;

α-butyl glucoside cocoate or α-butyl glucoside caprate, sold by the ULICE Co.

3/The esters of fatty acid and sugar that can be used as nonionic amphiphilic lipids in the nanoemulsion according to the invention are preferably solid at a temperature lower than or equal to 45° C. and can be chosen in particular in the group comprising the esters or the mixtures of esters of $C_8$ to $C_{22}$ fatty acids and sucrose, maltose, glucose or fructose, and the esters or the mixtures of esters of $C_{14}$ to $C_{22}$ fatty acids and methylglucose.

The $C_8$ to $C_{22}$ or $C_{14}$ to $C_{22}$ fatty acids forming the fatty moiety of the esters that can be used in the nanoemulsion of the invention contain a saturated or unsaturated linear alkyl chain having respectively 8 to 22 or 14 to 22 carbon atoms. The fatty moiety of the esters can be chosen in particular from among the stearates, behenates, arachidonates, palmitates, myristates, laurates, caprates and mixtures thereof. Preferably stearates are used.

As examples of esters or mixtures of esters of fatty acids and sucrose, maltose, glucose or fructose there can be cited sucrose monostearate, sucrose distearate, sucrose tristearate and mixtures thereof, such as the products sold by the Croda Co. under the names Crodesta F50, F70, F110 and F160, which respectively have an HLB (hydrophilic-lipophilic balance) of 5, 7, 11 and 16; and as examples of esters or mixtures of esters of fatty acids and methylglucose there can be cited the distearate of methylglucose and polyglycerol-3, sold by the Goldschmidt Co. under the name Tego-care 450. There can also be cited the monoesters of glucose or maltose, such as methyl O-hexadecanoyl-6-D-glucoside and O-hexadecanoyl-6-D-maltoside.

The ethers of fatty alcohol and sugar that can be used as nonionic amphiphilic lipids in the nanoemulsion according to the invention are solid at a temperature lower than or equal to 45° C. and can be chosen in particular in the group comprising the ethers or mixtures of ethers of $C_8$ to $C_{22}$ fatty alcohols and glucose, maltose, sucrose or fructose, and the ethers or the mixtures of ethers of $C_{14}$ to $C_{22}$ fatty alcohols and methylglucose. In particular, they are alkyl polyglucosides.

The $C_8$ to $C_{22}$ or $C_{14}$ to $C_{22}$ fatty alcohols forming the fatty moiety of the ethers that can be used in the nanoemulsion of the invention contain a saturated or unsaturated linear alkyl chain having respectively 8 to 22 or 14 to 22 carbon atoms. The fatty moiety of the ethers can be chosen in particular from among the decyl, cetyl, behenyl, arachidyl, stearyl, palmityl, myristyl, lauryl, capryl and hexadecanoyl moieties and mixtures thereof, such as cetearyl.

As examples of ethers of fatty alcohol and sugar there can be cited the alkyl polyglucosides such as decyl glucoside and lauryl glucoside sold, for example, by the Henkel Co. under the respective names of Plantaren 2000 and Plantaren 1200, cetostearyl glucoside, possibly mixed with cetostearyl alcohol sold, for example, under the name Montanov 68 by the Seppic Co., under the name Tego-care CG90 by the Goldschmidt Co. and under the name Emulgade KE3302 by the Henkel Co., as well as arachidyl glucoside, for example in the form of the mixture of arachidic and behenic alcohols with arachidyl glucoside, sold under the name Montanov 202 by the Seppic Co.

As nonionic amphiphilic lipid of this type there are used more particularly sucrose monostearate, sucrose distearate, sucrose tristearate and mixtures thereof, the distearate of methylglucose and polyglycerol-3. and the alkyl polyglucosides.

4/The fatty esters of glycerol that can be used as nonionic amphiphilic lipids in the nanoemulsion according to the invention, solid at a temperature lower than or equal to 45° C., can be chosen in particular in the group comprising the esters formed from at least one acid containing a saturated linear alkyl chain having 16 to 22 carbon atoms and 1 to 10 glycerol moieties. One or more of these fatty esters of glycerol can be used in the nanoemulsion of the invention.

These esters can be chosen in particular from among the stearates, behenates, arachidates, palmitates and mixtures thereof. Preferably stearates and palmitates are used.

As examples of the surfactant that can be used in the nanoemulsion of the invention there can be cited the monostearate, distearate, tristearate and pentastearate of decaglycerol (10 glycerol units) (CTFA names: polyglyceryl-10 stearate, polyglyceryl-10 distearate, polyglyceryl-10 tristearate, polyglyceryl-10 pentastearate), such as the products sold under the respective names of Nikkol Decaglyn 1-S, 2-S, 3-S and 5-S by the Nikko Co., and diglycerol monostearate (CTFA name: polyglyceryl-2 stearate), such as the product sold by the Nikko Co. under the name Nikkol DGMS.

The fatty esters of sorbitan that can be used as nonionic amphiphilic lipids in the nanoemulsion according to the invention, solid at a temperature lower than or equal to 45° C., can be chosen in particular in the group comprising the esters of $C_{16}$ to $C_{22}$ fatty acids and sorbitan and the esters of $C_{16}$ to $C_{22}$ fatty acids and oxyethylene sorbitan. They are formed from at least one fatty acid containing at least one saturated linear alkyl chain having respectively 16 to 22 carbon atoms, and from sorbitol or ethoxylated sorbitol. The oxyethylene esters generally contain 1 to 100 ethylene oxide units and preferably 2 to 40 ethylene oxide units (OE).

These esters can be chosen in particular from among the stearates, behenates, arachidates, palmitates and mixtures thereof. Preferably stearates and palmitates are used.

As examples of fatty esters of sorbitan and fatty esters of oxyethylene sorbitan that can be used in the nanoemulsion of the invention there can be cited sorbitan monostearate (CTFA name: sorbitan stearate), sold by the ICI Co. under the name Span 60, sorbitan monopalmitate (CTFA name: sorbitan palmitate), sold by the ICI Co. under the name Span 40, sorbitan (20 OE) tristearate (CTFA name: polysorbate 65), sold by the ICI Co. under the name Tween 65.

The ethoxylated fatty ethers that are solid at a temperature lower than or equal to 45° C. that can be used as nonionic amphiphilic lipids in the nanoemulsion according to the invention are preferably ethers formed from 1 to 100 ethylene oxide units and at least one fatty alcohol chain having 16 to 22 carbon atoms. The fatty chain of the ethers can be chosen in particular from among the behenyl, arachidyl, stearyl and cetyl moieties and mixtures thereof, such as cetearyl. As examples of ethoxylated fatty ethers there can be cited the ethers of behenic alcohol containing 5, 10, 20 and 30 ethylene oxide units (CTFA names: beheneth-5, beheneth-10, beheneth-20, beheneth-30), such as the products sold under the names Nikkol BB5, BB10, BB20 and BB30 by the Nikko Co., and stearyl alcohol ether containing 2 ethylene oxide units (CTFA name: steareth-2), such as the product sold under the name Brij 72 by the ICI Co.

The ethoxylated fatty esters that are solid at a temperature lower than or equal to 45° C. that can be used as nonionic amphiphilic lipids in the nanoemulsion according to the invention are esters formed from 1 to 100 ethylene oxide units and at least one fatty acid chain having 16 to 22 carbon atoms. The fatty chain of the esters can be chosen in particular from among the stearate, behenate, arachidate and palmitate moieties and mixtures thereof. As examples of ethoxylated fatty esters there can be cited the stearic acid ester containing 40 ethylene oxide units, such as the product sold under the name Myrj 52 by the ICI Co. (CTFA name: PEG-40 stearate), as well as the ester of behenic acid containing 8 ethylene oxide units (CTFA name: PEG-8 behenate), such as the product sold under the name Compritol HD5 ATO by the Gattefosse Co.

5/The block copolymers of ethylene oxide and propylene oxide that can be used as nonionic amphiphilic lipids in the nanoemulsion according to the invention can be chosen in particular from among the block copolymers of formula (V):

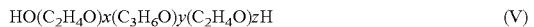

$$HO(C_2H_4O)x(C_3H_6O)y(C_2H_4O)zH \qquad (V)$$

in which x, y and z are integral numbers such that x+z ranges from 2 to 100 and y ranges from 14 to 60, and mixtures thereof, and more particularly from among the block copolymers of formula (V) having an HLB ranging from 2 to 16.

These block copolymers can be chosen in particular from among the poloxamers, and in particular from among poloxamer 231, such as the product sold by the ICI Co. under the name Pluronic L81 of formula (V), with x=z=6, y=39 (HLB 2); poloxamer 282, such as the product sold by the ICI Co. under the name Pluronic L92 of formula (V), with x=z=10, y=47 (HLB 6); and poloxamer 124, such as the product sold by the ICI Co. under the name Pluronic L44 of formula (V), with x=z=11, y=21 (HLB 16).

As nonionic amphiphilic lipids there can also be cited the mixtures of nonionic surfactants described in European Patent A 705593, incorporated here by reference.

Among the nonionic amphiphilic lipids there can be used in particular:

PEG 400 isostearate or PEG-8 isostearate (containing 8 moles of ethylene oxide),
diglyceryl isostearate,
polyglycerol monolaurate containing 2 glycerol units and polyglycerol stearates containing 10 glycerol units.
sorbitan oleate,
sorbitan isostearate and mixtures thereof.

The nonionic amphiphilic lipids can be present in the nanoemulsion according to the invention in a content ranging from 0.2% to 12% by weight relative to the total weight of the composition, and preferably ranging from 0.2% to 8% by weight, and preferentially ranging from 0.2% to 6% by weight.

The cationic amphiphilic lipids are chosen from among the list given hereinafter.

They are present in the nanoemulsions of the invention in concentrations ranging preferably from 0.01 to 6% by weight relative to the total weight of the nanoemulsion, and more particularly from 0.2 to 4% by weight.

Oils:

The oily phase of the nanoemulsion according to the invention comprises at least one oil. The oils that can be used in the nanoemulsions of the invention are preferentially chosen in the group formed by:

the oils of animal or vegetable origin, formed by esters of fatty acids and polyols, particularly the liquid triglycerides, such as sunflower, corn, soy, avocado, jojoba, pumpkin, grapeseed, sesame and hazelnut oils, fish oils, glycerol tricaprocaprylate, or the vegetable or animal oils of formula $R_9COOR_{10}$, in which $R_9$ represents the residue of a higher fatty acid containing 7 to 29 carbon atoms and $R_{10}$ represents a linear or branched hydrocarbon chain containing 3 to 30 carbon atoms, particularly alkyl or alkenyl, examples being purcellin oil or liquid jojoba wax;

natural or synthetic essential oils such as, for example, eucalyptus, lavandin, lavender, vetiver, litsea cubeba, citron, sandalwood, rosemary, chamomile, savory, nutmeg, cinnamon, hyssop, caraway, orange, geraniol, cade and bergamot oil;

synthetic oils such as parleam oil, polyolefins and liquid carboxylic acid esters;

mineral oils such as hexadecane, isohexadecane and paraffin oil;

halogenated oils, especially fluorocarbons such as fluoro amines, for example perfluorotributylamine, fluorinated hydrocarbons, for example perfluorodecahydronaphthalene, fluoro esters and fluoro ethers;

volatile or non-volatile silicone oils.

The polyolefins that can be used as synthetic oils are in particular the poly-α-olefins and more particularly those of the hydrogenated or non-hydrogenated polybutene type, and preferably hydrogenated or non-hydrogenated polyisobutene.

The liquid carboxylic acid esters that can be used as synthetic oils can be esters of mono-, di-, tri- or tetracarboxylic acids. The total carbon number of the esters is generally greater than or equal to 10 and preferably less than 100, and more particularly less than 80. Such esters are in particular the monoesters of saturated or unsaturated, linear or branched $C_1$ to $C_{26}$ aliphatic acids and saturated or unsaturated, linear or branched $C_1$ to $C_{26}$ aliphatic alcohols, the total carbon number of the esters generally being greater than or equal to 10. It is also possible to use the esters of $C_4$ to $C_{22}$ di- or tricarboxylic acids and $C_1$ to $C_{22}$ alcohols and the esters of $C_2$ to $C_{26}$ mono-, di- or tricarboxylic acids and di-, tri-, tetra or pentahydroxy alcohols.

Among the esters cited in the foregoing, there are preferably used alkyl palmitates such as ethyl palmitate, isopropyl palmitate, ethyl-2-hexyl palmitate and 2-octyldecyl palmitate; alkyl myristates such as isopropyl myristate, butyl myristate, cetyl myristate and 2-octyldodecyl myristate; alkyl stearates, such as hexyl stearate, butyl stearate and isobutyl stearate; alkyl malates, such as dioctyl malate; alkyl laurates, such as hexyl laurate and 2-hexyldecyl laurate; isononyl isononanate; cetyl octanoate.

Advantageously, the nanoemulsion according to the invention contains at least one oil of molecular weight greater than or equal to 400, especially ranging from 400 to 10,000, better ranging from 400 to 5000, or even ranging from 400 to 5000. The oils of molecular weight greater than or equal to 400 can be chosen from among the oils of animal or vegetable origin, the mineral oils, the synthetic oils and the silicone oils and mixtures thereof. As oils of this type there can be cited, for example, isocetyl palmitate, isocetyl stearate, avocado oil and jojoba oil.

The nanoemulsions according to the invention contain a quantity of oily phase (oil and other fatty substances not including the amphiphilic liquid) ranging preferably from 2 to 40% by weight relative to the total weight of the nanoemulsion, and more particularly from 4 to 30% by weight and preferentially from 4 to 20% by weight.

The oily phase and the amphiphilic lipids (nonionic and ionic amphiphiles) are preferably present in the nanoemulsion according to the invention in a weight ratio of the quantity of oily phase to the quantity of amphiphilic liquid that ranges from 3 to 10 and preferentially from 3 to 6. By "quantity of oily phase" there is understood here the total quantity of the constituents of this oily phase without including the quantity of amphiphilic liquids.

Besides the urea derivatives of formula (I) described previously, the nanoemulsions according to the present invention can contain solvents, in particular to improve the transparency of the composition if necessary.

These solvents are preferably chosen in the group formed by:
$C_1$ to $C_8$ lower alcohols, such as ethanol;
glycols, such as glycerol, propylene glycol, 1,3-butylene glycol, dipropylene glycol and the polyethylene glycols containing 4 to 16 and preferably 8 to 12 ethylene oxide units;
sugars, such as glucose, fructose, maltose, lactose and sucrose.

These solvents can be used as mixtures. When they are present in the nanoemulsion of the invention, they can be used in concentrations ranging preferably from 0.01 to 30% by weight relative to the total weight of the nanoemulsion, and better from 5 to 20% by weight relative to the total weight of the nanoemulsion. The quantity of alcohol(s) and/or of sugar(s) preferably ranges from 5 to 20% by weight relative to the total weight of the nanoemulsion and the quantity of glycols preferably ranges from 5 to 15% by weight relative to the total weight of the nanoemulsion.

Preparation Method:

The method for preparation of a nanoemulsion such as defined in the foregoing comprises mixing the aqueous phase containing the urea derivative with the oily phase under vigorous agitation at a temperature ranging from 10° C. to 80° C., performing a step of high-pressure homogenization at a pressure above $5 \cdot 10^7$ Pa and if necessary adding the polymer used. According to a preferred embodiment of the invention, another step of high-pressure homogenization at a pressure above $5 \cdot 10^7$ Pa is then performed. The high-pressure homogenization is preferably performed at a pressure ranging from $6 \cdot 10^7$ to $18 \cdot 10^7$ Pa. The shear preferably ranges from $2 \cdot 10^6 \, s^{-1}$ to $5 \cdot 10^8 \, s^{-1}$ and better from $1 \cdot 10^8 \, s^{-1}$ to $3 \cdot 10^8 \, s^{-1}$ ($s^{-1}$ denotes seconds$^{-1}$). Such a method makes it possible to obtain nanoemulsions that are compatible with heat-sensitive active compounds and that can contain oils, and especially perfumes containing fatty substances, without denaturing them.

Nanocapsules

The nanocapsules useful in the invention are those described in Patent Applications EP 0447318, EP 0557489, EP 0780115, EP 1025901, EP 1029587, EP 1034839, EP 1414390, FR 2830776, EP 1342471, FR 2848879 and FR 04/50057.

Nanocapsules are core-shell particles having an oily core and a polymer shell. The different applications cited in the foregoing relate to different polymer families and different methods for obtaining same. The size of the capsules is always less than 1 µm, and it is possible to obtain sizes less than 80 nm. These particles can be coated by a lamellar liquid crystal phase, most often composed of a lecithin or of a dimethicone copolyol. The coating must be composed of an amphiphilic lipid capable of spontaneously forming a lamellar liquid crystal phase upon contact with water. It is to this amphiphilic lipid capable of forming a lamellar phase that there will be added the cationic surfactant that will impart a positive zeta potential to the particles (the nanocapsule). The weight ratio between the amphiphilic lipid forming the lamellar phase and the cationic surfactant will range between 99/1 and 75/25.

The cationic surfactants that can be used are those listed hereinafter.

Organic Particles

The organic particles of the invention are solid nanospheres without internal cavity, formed by different methods (dispersion in water, nanoprecipitation, microemulsion, etc.) and are composed of at least one polymer or of at least one copolymer or of a mixture thereof. The particle is cationic, with the zeta potential defined in the foregoing, either because the polymer or copolymer or the polymers or copolymers are cationic, or because they are nonionic and a cationic surfactant such as described hereinafter is used. Relative to the polymer, the proportion of cationic surfactant will range between 0 and 25%.

Inorganic Particles

The cationic inorganic particles of the invention can be based, for example, on silica, $TiO_2$, ZnO, alumina, etc. As an example, there will be cited alumina particles in colloidal dispersion in water, such as Nanomer 2 of Nalco. Clariant and Grace also propose particles of this type.

Cationic Surfactants that can be Used for Preparation of the Cationic Particles of the Invention The cationic surfactants that can be used according to the invention are listed hereinafter. This list is non-limitative.

The cationic amphiphilic lipids are preferably chosen in the group formed by the quaternary ammonium salts, the fatty amines and the salts thereof.

The quaternary ammonium salts are, for example:
those having the following general formula (IV):

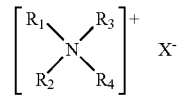

in which the radicals R1 to R4, which can be identical or different, represent a linear or branched aliphatic radical containing 1 to 30 carbon atoms, or an aromatic radical such as aryl or alkylaryl. The aliphatic radicals can contain hetero atoms, such as, in particular, oxygen, nitrogen, sulfur and halogens. The aliphatic radicals are chosen, for example, from among the alkyl, alkoxy, polyoxyalkylene(C2 to C6), alkylamide, alkyl(C12 to C22)amidoalkyl(C2 to C6), alkyl (C12 to C22) acetate and hydroxyalkyl containing approximately 1 to 30 carbon atoms; X is an anion chosen in the group of halides, phosphates, acetates, lactates, alkyl(C2 to C6) sulfates, alkyl- or alkylarylsulfonates, the quaternary ammonium salts of imidazolinium, such as, for example, that of the following formula (V):

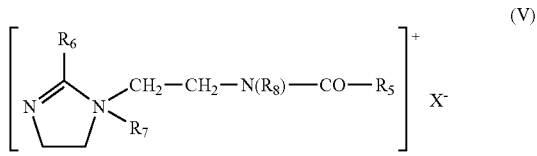

in which R5 represents an alkenyl or alkyl radical that contains 8 to 30 carbon atoms and is derived, for example, from tallow fatty acids, R6 represents a hydrogen atom, a C1 to C4 alkyl radical or an alkenyl or alkyl radical containing 8 to 30 carbon atoms, R7 represents a C1 to C4 alkyl radical, R8 represents a hydrogen atom or a C1 to C4 alkyl radical, X is an anion chosen in the group of halides, phosphates, acetates, lactates, alkyl sulfates and alkyl- or alkylarylsulfonates. Preferably, R5 and R6 denote a mixture of alkenyl or alkyl radicals that contain 12 to 21 carbon atoms and are derived, for example, from tallow fatty acids, R7 denotes methyl and R8 denotes hydrogen. Such a product is sold, for example, under the name "REWOQUAT W 75" by the REWO Co., the quaternary diammonium salts of formula (VI):

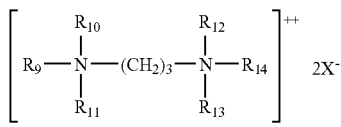

in which R9 denotes an aliphatic radical containing approximately 16 to 30 carbon atoms, R10, R11, R12, R13 and R14, identical or different, are chosen from among hydrogen or an alkyl radical containing 1 to 4 carbon atoms, and X is an anion chosen in the group of halides, acetates, phosphates, nitrates and methyl sulfates. Such quaternary diammonium salts comprise in particular propane tallow diammonium dichloride;

the quaternary ammonium salts containing at least one ester function

The quaternary ammonium salts that contain at least one ester function and that are usable according to the invention are, for example, those of the following formula (VII):

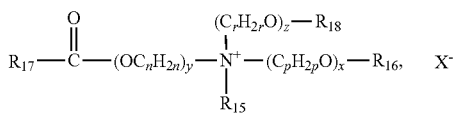

in which:

R15 is chosen from among the C1 to C6 alkyl radicals and the C1 to C6 hydroxyalkyl or dihydroxyalkyl radicals;

R16 is chosen from among:
the radical

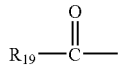

linear or branched, saturated or unsaturated C1 to $C_2$-2 hydrocarbon radicals R20,
a hydrogen atom,
R18 is chosen from among:
the radical

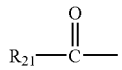

linear or branched, saturated or unsaturated C1 to C6 hydrocarbon radicals R22,
a hydrogen atom,
R17, R19 and R21, identical or different, are chosen from among the linear or branched, saturated or unsaturated C7 to C21 hydrocarbon radicals:
n, p and r, identical or different, are integers equal to 2 to 6;
y is an integer equal to 1 to 10;
x and z, identical or different, are integers equal to 0 to 10;
X— is a simple or complex, organic or inorganic anion;
with the provisos that the sum of x+y+z is equal to 1 to 15, that when x is equal to 0 then R16 denotes R20 and that when z is equal to 0 then R18 denotes R22.

The alkyl radicals R15 can be linear or branched and more particularly linear.

Preferably R15 denotes a methyl, ethyl, hydroxyethyl or dihydroxypropyl radical, and more particularly a methyl or ethyl radical. Advantageously, the sum of x+y+z is equal to 1 to 10.

When R16 is a hydrocarbon radical R20, it can be long with 12 to 22 carbon atoms or short with 1 to 3 carbon atoms.

When R18 is a hydrocarbon radical R22, it preferably has 1 to 3 carbon atoms.

Advantageously, R17, R19 and R21, identical or different, are chosen from among the linear or branched, saturated or unsaturated C11 to C21 hydrocarbon radicals, and more particularly from among the linear or branched, saturated or unsaturated C11 to C21 alkyl and alkenyl radicals.

Preferably x and z, identical or different, are equal to 0 or 1.
Advantageously, y is equal to 1.
Preferably, n, p and r, identical or different, are equal to 2 or 3 and even more particularly are equal to 2.

The anion is preferably a halide (chloride, bromide or iodide) or an alkyl sulfate, more particularly methyl sulfate. However, it is possible to use methanesulfonate, phosphate, nitrate, tosylate, an anion derived from an organic acid such as acetate or lactate, or any other anion that is compatible with ammonium and has an ester function.

The anion X— is even more particularly chloride or methyl sulfate.

More particularly, there are used the ammonium salts of formula (VII) in which:
R15 denotes a methyl or ethyl radical,
x and y are equal to 1;
z is equal to 0 or 1;
n, p and r are equal to 2;

R16 is chosen from among:
the radical

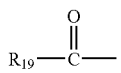

the methyl, ethyl or C14 to C22 hydrocarbon radicals
a hydrogen atom;
R18 is chosen from among:
the radical

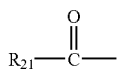

a hydrogen atom;
R17, R19 and R21, identical or different, are chosen from among the linear or branched, saturated or unsaturated C13 to C17 hydrocarbon radicals, and preferably from among the linear or branched, saturated or unsaturated C13 to C17 alkyl and alkenyl radicals.

Advantageously, the hydrocarbon radicals are linear.

As examples there can be cited the compounds of formula (VII) such as the salts (especially chloride or methyl sulfate) of diacyloxyethyldimethylammonium, of diacyloxyethylhydroxyethylmethylammonium, of monoacyloxyethyldihydroxyethylmethylammonium, of triacyloxyethylmethylammonium, of monoacyloxyethylhydroxyethyldimethylammonium and mixtures thereof. The acyl radicals preferably have 14 to 18 carbon atoms and originate more particularly from a vegetable oil such as palm or sunflower oil.

When the compound contains a plurality of acyl radicals, these radicals may be identical or different.

These products are obtained, for example, by direct esterification of triethanolamine, triisopropanolamine, alkyldiethanolamine or alkyldiisopropanolamine, which may be oxyalkenated on the fatty acids or on mixtures of fatty acids of vegetable or animal origin or by transesterification of their methyl esters. This esterification is followed by quaternization by means of an alkylating agent such as an alkyl halide (preferably methyl or ethyl), a dialkyl sulfate (preferably methyl or ethyl), methyl methylsulfonate, methyl paratoluenesulfonate, or glycol or glycerol chlorohydrin.

Such compounds are sold, for example, under the names DEHYQUART by the HENKEL Co., STEPANQUAT by the STEPAN Co., NOXAMIUM by the CECA Co. and REWOQUAT WE 18 by the REWOWITCO Co.

The composition according to the invention preferably contains a mixture of salts of mono-, di- and triesters of quaternary ammonium, wherein the diester salts represent the majority by weight.

As the mixture of ammonium salts there can be used, for example, the mixture containing 15 to 30% by weight of acyloxyethyldihydroxyethylmethylammonium methyl sulfate, 45 to 60% of diacyloxyethylhydroxyethylmethylammonium methyl sulfate and 15 to 30% of triacyloxyethylmethylammonium methyl sulfate, the acyl radicals having 14 to 18 carbon atoms and originating from palm oil, which may be partly hydrogenated. There can also be used the ammonium salts containing at least one ester function described in U.S. Pat. Nos. 4,874,554 and 4,137,180.

Among the quaternary ammonium salts of formula (IV) there are preferred, on the one hand, the tetraalkylammonium chlorides such as, for example, the dialkyldimethylammonium or alkyltrimethylammonium chlorides, in which the alkyl radical contains approximately 12 to 22 carbon atoms, especially behenyltrimethylammonium, distearyldimethylammonium, cetyltrimethylammonium and benzyldimethylstearylammonium chlorides, or else, on the other hand, stearamidopropyldimethyl(myristyl acetate)ammonium chloride, sold under the name "CERAPHYL 70" by the VAN DYK Co.

According to the invention, behenyltrimethylammonium chloride or bromide and CTAB (cetyltrimethylammonium bromide) are the most particularly preferred quaternary ammonium salts.

The fatty amines of the invention correspond to the general formula:

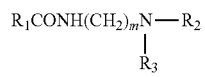

$R_1$ is a saturated or unsaturated, branched or linear hydrocarbon chain having between 8 and 30 and preferably between 10 and 24 carbon atoms.

$R_2$ and $R_3$ are selected independently from among saturated or unsaturated, branched or linear hydrocarbons having between 1 and 10 and preferably between 1 and 4 carbon atoms.

$R_2$ and $R_3$ can also correspond to a hydrogen atom H, again independently of one another.

M is between 1 and 10 and preferably between 1 and 5.

As non-limitative examples there will be cited: stearylamine, stearate aminoethylethanolamide, stearyl diethanolamide, stearate diethylenetriamine, stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, arachidamidoethyldimethylamine.

As commercially available fatty amine there can be cited Incromine BB of Croda, Amidoamine MSP of Nikkol and the Lexamines of Inolex.

As other fatty amines there can be cited, as examples, stearylamine, stearate aminoethylethanolamide, stearyl diethanolamide and stearate diethylenetriamine, which Sabo sells among others with the Sabomina series.

There will also be cited the fatty amine acetates, such as the Acetamine series of Kao Corp.

These fatty amines can also be ethoxylated, such as Berols 380, 390, 453 and 455, the Ethomeens of Akzo Nobel or Marlazins L10, OL2, OL20, T15/2 and T50 of Condea Chemie.

The particles of the present invention can be introduced into all medicinal supports intended for cosmetic, dermatological and ophthalmic purposes. As examples, there will be cited lotions, serums, gels and all types of emulsions.

The double stranded RNA oligonucleotides (or else dsRNA for double stranded RNA, siRNA for short interfering RNA) that can be used according to the present invention are double stranded nucleic acid fragments capable of totally or partly inhibiting gene expression in a eukaryotic cell, these double stranded RNA oligonucleotides generally containing between 12 and 40 nucleotides, preferentially from 20 to 25 nucleotides. These double stranded oligonucleotides are composed of one sense strand and one anti-sense strand, corresponding to the sequence of the target messenger RNA to be degraded. The double stranded RNA oligonucleotide has free or unpaired ends of 2 to 6 nucleotides.

It will be possible for the double stranded RNA oligonucleotides according to the invention to be double stranded RNA oligonucleotides containing one or more nucleotides modified by substitution, deletion or insertion, and these modifications will be such that the oligonucleotide sequence of the double stranded RNA will permit it to recognize specifically a fragment of the target mRNA of the degradation mechanism.

It will also be possible for the oligonucleotides of the double stranded RNA to have a modified skeleton that, for example, imparts better stability to it.

For example, the phosphodiester bonds of natural RNA strands can be modified to include at least one nitrogen or sulfur atom. In addition, the double stranded RNA oligonucleotides according to the invention can comprise bases other than the 4 classical bases.

The double stranded structure of the double stranded RNA oligonucleotide can be obtained by pairing two complementary single RNA strands or by a unique "self-complementary" single RNA strand, or in other words one comprising two fragments of complementary sequences that can be paired by folding the single strand to form a double helix.

Examples of double stranded RNA oligonucleotides are described in International Patent Applications WO 00/44895, WO 01/36646, WO 99/32619, WO 01/29058, WO 00/44914 or else WO 03/101376.

They may also be oligonucleotides of the double stranded RNA known as "stealth RNA", such as those sold by the Invitrogen Co. and described in US Patent Applications 2004014956 and 2004054155, which are oligonucleotides of double stranded RNA that can be modified in such a way that, as a non-limitative example, one of its ends contains a 2'-O-methyl group.

The double stranded RNA oligonucleotides can be synthesized manually or automatically by numerous in vivo or in vitro synthesis methods as known in the art.

The in vitro synthesis methods can be chemical or enzymatic, for example by using a polymerase RNA (such as T3, T7 or SP6, for example), which will achieve transcription of a chosen DNA (or cDNA) sequence model.

Numerous methods for in vivo synthesis of double stranded RNA are described in the literature. They can be achieved in various cellular types of bacteria or higher organisms (Sambrook et al. Molecular Cloning, A Laboratory Manual, Second Edition (1989), DNA cloning, volume I and II, D. N. Glover (ed. 1985), Oliginucleotide Synthesis, M. J. Gaits (ed. 1984), Nucleic Acid Hybridation, B. D. Hames and S. J. Higgins (ed. 1984), Transcription and Translation B. D. Hames and S. J. Higgins (ed. 1984), Animal Cell Culture, R. I. Freshney (ed. 1986), Immobilised Cells and Enzymes, IRL Press (1986), B. Pertal, A Practical Guide to Molecular Cloning (1984), Gene Transfer Vectors for Mammalian Cells, J. H. Miller and M. P. Calos, Cold Spring Harbor Laboratory (ed. 1987), Methods in Enzymology, vol. 154, Wu and Grossman, and 155, Wu, Mayer and Walker (1987), Immunochemical Methods in Cell and Molecular Biology, Academic Press, London, Scopes (1987), Protein Purification: Principle and Practice, $2^{nd}$ ed., Springer-Verlag, N.-Y. and Handbook of Experimental Immunology, vol. I-IV, C. D. Weir and C. C. Blackwell (1986)). Reference can also be made to the synthesis methods described in Patent Applications WO01/36646, WO01/75164 and US20030088087.

The compositions can also contain one or more ingredients, such as carriers, active agents, etc suitable for cosmetic and/or ocular applications. Such ingredients are well-known in the art.

A skin model according to the present invention is a reconstructed skin model composed of, for example, an epidermis reconstructed from skin keratinocytes, or derived from the external sheath of the hair follicle, an epidermis reconstructed on a de-epidermized inert dermis (DED), a dermis and a reconstructed epidermis, or a reconstructed epidermis that integrates non-keratinocytic cells such as Langerhan's cells and melanocytes. As an example there can be cited the Episkin® reconstructed skin (epidermis) model. The EpiSkin models are obtained by culturing adult human keratinocytes on a collagen support under conditions that permit their terminal differentiation and reconstruction of an epidermis with a functional horny layer. These different in vitro models are described in particular in the following references: Asselineau D. et al., *Exp Cell Res* 1985 August; 159(2):536-539; Lenoir M C et al. *Dev Biol* 1988 December; 130 (2):610-20; Regnier M. et al. *J Invest Dermatol* 2000 January; 114 (1): 220-220; Regnier M: et al. *J Invest Dermatol* 1997 October; 109 (4):510-2; Regnier M. et al. *In Vitro Cell Dev Biol* 1988 July; 24 (7):625-32; Cohen C. et al. *J Invest Dermatol* 1995 January; 104 (1):159-159; Tinois E. et al., *Exp Cell Res* 1991 April; 193(2):310-319.

The skin models can also be ex vivo skins maintained in viable condition, such as Episkin®, SkinEthic®, Matek® and Natskin®.

A second object of the present invention relates to the use of a composition comprising at least one double stranded RNA oligonucleotide associated with at least one cationic particle of size less than or equal to 1 µm, of zeta potential between 10 and 80 mV, chosen from among surfactant micelles, block polymer micelles, liposomes of nonionic and cationic surfactants, niosomes, oleosomes, particles of nanoemulsions, nanocapsules, organic particles or inorganic particles for the treatment of skin models, more particularly for partial or total inhibition of protein expression by the cells of a skin model. Therefore, methods of inhibiting protein, partially or totally, can be accomplished by administering or applying the compositions of dsRNA and cationic particles to the cells of the skin and/or skin model.

The use of these reconstructed skin models therefore makes it possible, by topical or systemic application of vectorized siRNA, to:
  validate a chosen target by studying the effects produced by the decrease of protein expression in the skin;
  reproduce pathological skin models (example: targeting of cytokeratins CK5 or CK14 to reproduce epidermolysis bullosa simplex; or of CK1, CK2e or CK10 for epidermolytic hyperkeratoses, etc.)
  normalize the reconstructed skin models by decreasing protein expression that is excessive compared with the normal skin (example: vimentine, CK17, etc.)
As a non-limitative example of protein whose expression it will be possible to inhibit there can be cited:
  growth factors EGF, TNF-αc, TGF, endothelin, NGF, HGF, IGF, VEGF;
  cytokines, for example of IL1, IL6, IL8, etc., type;
  receptors of EDFr, TGFr, PAR, PPAR, FXR, RXR, CB1R, CB2R, VR1, CRAB2, etc., type;
  calcium binding proteins of calmodulin, CLP, CLSP type, those of the family of S100 proteins, such as S100A8, S100A9, S100A7, etc.;

calcineurin;
transglutaminases, for example transglutaminases 1, 3 or 5;
proteins that ensure intercellular cohesion and linkage, such as occludins, laminins, caveolins, desmogleins, desmocollins, comeodesmosins, plakoglobins, desmoplakins, etc.;
enzymes involved in post-translational modifications of proteins such as phosphatases or protein phosphatases, for example calcineurin, phosphorylases, protein kinases (e.g., PKC), glucosyl transferases, peptidyl-arginine-deiminases, etc.;
proteases (MMP, for example 1, 2, 3 and 9, elastases, aspartic acid proteases such as cathepsin-E and cathepsin-D, cystein proteases of the cathepsin-L, B or H type, cathepsin L2, SCCL, chymotrypsin equivalents, for example of the SCCE (kallicrein 7) type, trypsin-like, for example of the SCTE (kallicrein 5) type, urokinase, SASPase, caspase, more specifically caspase 14, calpains, proteases of the subtilisin-like proprotein convertase type involved in the hydrolysis of filaggrin, such as furin, PACE4, PC5/6 and PC7/8, proteases of the serine protease family of the transmembrane type, for example matriptase and/or their endogenous inhibitors such as TIMP, PAI1, PAI2, antileukoprotease, elafin, LEKTI, cystatin A, cystatin M/E, etc.;
exoglycosidases and endoglycosidases, for example of the heparanase type, hyaluronidases, chondroitinases, aspartyl glucosamimidase, B-glycosidase, a-glycosidases, etc., and their endogenous inhibitors;
enzymes of lipid metabolism, such as HMGCoA reductase, cholesterol sulfatases or sulfotransferases, sphingomyelinases, ceramidases, etc.;
enzymes involved in melanogenesis, such as tyrosinase, TRP-1 or -2, SOX10, MITF, pMel17, PAX3, POMC, MC1R, α-MSH, etc.
enzymes involved in oxidative stress, such as SOD-1, SOD-2, glutathion peroxidase, catalase, thio-redoxin reductase, glutathion reductase, cytochrome P450, sulfotransferase, gamma glutamyl synthetase, etc.;
enzymes of eicosanoid metabolism, such as, for example, cyclooxygenases, lipoxygenases, phospholipases, 15-PGDH, etc.;
enzymes of hormonal metabolism, such as type 1 or type 25-α-reductase;
matrix proteins of the elastin, collagen, etc. type;
keratinocyte differentiation proteins of the cytokeratin type;
proteins involved in hydration of the skin such as filaggrin, aquaporins, etc.;
proteins involved in the antibacterial defenses of the skin, hBD2, hBD3, dermcidin, RNase 7, etc.;

Other non-limitative examples of proteins or peptides whose expression and/or activity is intended to be inhibited are reported in "Textbook of Dermatology", eds. R H Champion, J L Burton, D A Burns, S M Breathnach, sixth edition, 1998, Blackwell Science Ltd ISBN 0-632-03796-2.

The person skilled in the art will choose a double stranded RNA oligonucleotide concentration appropriate for the intended use and the activity of the chosen oligonucleotide. It will be possible, without this being limitative, for the double stranded RNA oligonucleotide concentration to be between 10 pM and 1 µM.

Methods of transfection currently used for studies on cell cultures in monolayers can be either Lipofectamine 2000 (Invitrogen), JetSI (Qbiogene), RNAiFext (Qiagen), etc., or viral particles of the retrovirus, lentivirus, adenovirus, etc. type. However, these transfection solutions are toxic, costly and not readily available, especially because the viral particles necessitate extremely prolonged use.

In addition, as far as Lipofectamine 2000 or the other chemical transfection agents are concerned, they have not been previously demonstrated to permit penetration of siRNA into the cells of a three-dimensional in vitro model such as the reconstructed skins (Episkin, Matek, Skinethic, etc.).

The Applicant has been able to show that the particles of the present invention permit the siRNA to penetrate into the epidermal cells of a reconstructed skin model (see Example 2).

Thus, according to a third object, the present invention relates to a method for preparation of a skin model by administering or applying, in the culture medium of the said model, a composition comprising at least one double stranded RNA oligonucleotide associated with at least one cationic particle of size less than or equal to 1 µm, of zeta potential between 10 and 80 mV, chosen from among surfactant micelles, block polymer micelles, liposomes of nonionic and cationic surfactants, niosomes, oleosomes, particles of nanoemulsions, nanocapsules, organic particles or inorganic particles.

It will be additionally possible for the method to comprise a supplementary step of application of an occlusive system; a preliminary step aimed at reducing the proportion of Ca2+ in the culture medium of the skin model; and a treatment for which the permeability of the skin model is increased at the same time as the composition is being applied.

Most often, the particle suspension associated with the siRNA is applied on the surface of the model for a contact time of at least 2 h. If necessary, the surface can be washed before analysis.

In order to facilitate penetration of the particles associated with the siRNA, it will be possible to modify the function of the model during pretreatment and/or treatment by:
    using an occlusive system such as, for example, an application of vaseline after application of the particles associated with the siRNA (once the surface is dry), or covering the surface of the model by a sheet of occlusive polymer. Care will be taken that the means used does not damage the surface of the model;
    before deposition of the particles associated with the siRNA, it will be possible to reduce the proportion of Ca2+ either by changing the medium (0.10 to 0.75 mM instead of 1.5 mM) or by adding a chelating agent. That has the effect of decreasing the intermembrane adhesion, thus increasing the permeability of the model (Effects of extra- and intracellular calcium concentration on DNA replication, lateral growth, and differentiation of human epidermal cells in culture. Virchows Arch B *Cell Pathol Incl Mol Pathol.* 1990; 59(1):17-25);
    iontophoresis, electroporation and all known methods that make it possible to increase the permeability of the model.

It will be possible to achieve application either on all types of cutaneous cells (keratinocytes, melanocytes, fibroblasts, etc.) in a monolayer before they are or are not integrated into a three-dimensional model, either topically on the three-dimensional model or systemically in the three-dimensional model subjected to emersion conditions by addition to the culture medium. As an alternative, it will also be possible to immerse the three-dimensional model in a medium containing the particles associated with the siRNA, in order to ensure transfection.

Figure 1B:
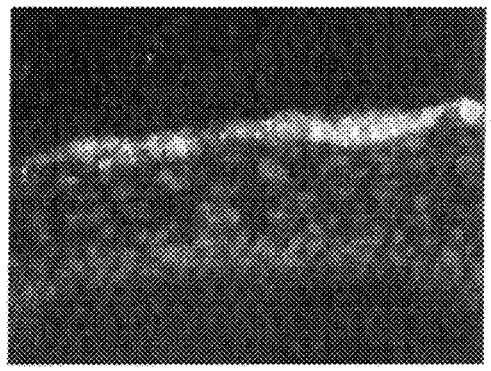

The following figures illustrate the tests described in Example 2:

I. Cell Targeting in Episkin—day 6
FIG. 1A: Block-It Fluorescent Oligo (DAPI)
FIG. 1B: Block-It Fluorescent Oligo+Lipofectamine 2000 (DAPI)
FIG. 1C: Block-It Fluorescent Oligo+E2 (×40, DAPI)
FIG. 1D: E2 (×40, DAPI)
FIG. 1E: Block-It Fluorescent Oligo+E2 (×100, DAPI)
FIG. 1F: Block-It Fluorescent Oligo+E2 (×100)
II. Cell Targeting in Episkin—day 13
FIG. 2A: Block-It Fluorescent Oligo (×40, DAPI)
FIGS. 3A-3H and FIGS. 4A-D: visualization of the effect of the formulation comprising octyl glucoside and CTAB in different concentrations on the viability of HaCaT cells.

The invention will now be illustrated by the following non-limiting examples.

In these examples, the amounts are indicated as percentages by weight.

EXAMPLE

Formulation

Cationic Micelles:
A.1. Octyl β-glucoside/cetyltriammonium bromide in the molar ratio of 5/1, from which mixture there are then prepared four compositions in the dilution ratios shown below:
E1: 100 mM in distilled water
E2: 50 mM in distilled water
E3: 25 mM in distilled water
E4: 12.5 mM in distilled water
The 2 surfactants (nonionic+cationic) are solubilized in distilled water. A suspension of siRNA (20 μM) is added in a volume (siRNA:micelles) of between 1:1 and 1:9, thus proportionally reducing the micellar concentration.
A.2. Micelles of decyl β-glucoside/behenyltriammonium chloride in the molar ratio of 5/1 in distilled water. The same concentrations are prepared as in the preceding example.

Cationic Liposomes

Example 1: "Fluid" Vesicles

| | |
|---|---|
| PEG 400 isostearate | 5.5% |
| Behenyltriammonium chloride | 0.5% |
| Distilled water | qsp 100 |

Example 2: "Rigid" Vesicles

| | |
|---|---|
| Sorbitan palmitate | 2.75% |
| Cholesterol | 2.75% |
| Behenyltriammonium chloride | 0.5% |
| Distilled water | qsp 100 |

These two examples of liposome suspensions are prepared by dialysis. The constituent lipids of the vesicles are solubilized in an aqueous solution of octyl β-glucoside. This solution is then dialyzed against water for 72 h.

The suspension of siRNA is added, making the vesicle concentration around 0.3% of lipid, this value being merely indicative.

Cationic Oleosomes

| Oily phase | |
|---|---|
| Sucrose mono/di-stearate sold by Stéarainerie Dubois | 0.45% |
| Sorbitan (4 OE) stearate (Tween 61 Uniqema) | 0.30% |
| Behenyltriammonium chloride | 0.21% |
| Vitamin E acetate | 0.5% |
| Jojoba oil | 0.5% |
| Stearyl heptanoate | 1% |
| Volatile silicone oil SE | 1% |
| Vitamin F glyceride | 0.5% |
| Preservative | 0.02% |
| BHT | 0.01% |

| Aqueous phase | |
|---|---|
| Distilled water | qsp 100 |
| Preservative | 0.1% |

This dispersion is prepared by high-pressure homogenization in order to obtain a particle size of approximately 170 nm. There is then added a suspension of siRNA (20 μM) in ratios ranging from 1:1 to 1:20 (siRNA:oleosomes). The siRNA will then become complexed on the surface of the particles.

Cationic Nanocapsules

| Organic phase | |
|---|---|
| Polycaprolactone (MW: 50000) | 1% |
| Vitamin E | 1% |
| Dimethicone copolyol DC2 5695 (Dow Corning) | 0.5% |
| Behenyltriammonium chloride | 0.21% |
| Acetone | 200 ml |

| Aqueous phase | |
|---|---|
| Pluronic F68 | 0.5% |
| Distilled water | 200 ml |

The organic phase is introduced into the aqueous phase with agitation. The acetone and 100 ml of the aqueous phase are then evaporated to obtain the suspension of nanocapsules, which have a size of 220 nm. There is then added a suspension of siRNA (20 μM) in ratios ranging from 1:1 to 1:20 (siRNA: nanocapsules). The siRNA will then become complexed on the surface of the particles.

Organic Nanoparticles

| Organic phase | |
|---|---|
| Polyethylene adipate (Scientific Polymer Products) | 2% |
| Dimethicone copolyol DC2 5695 (Dow Corning) | 0.5% |
| Behenyltriammonium chloride | 0.21% |
| Acetone | 200 ml |

| Aqueous phase | |
|---|---|
| Pluronic F68 | 0.5% |
| Distilled water | 200 ml |

The organic phase is introduced into the aqueous phase with agitation. The acetone and 100 ml of the aqueous phase are then evaporated to obtain the suspension of nanoparticles, which have a size of 180 nm. There is then added a suspension of siRNA (20 μM) in ratios ranging from 1:1 to 1:20 (siRNA: nanoparticles). The siRNA will then become complexed on the surface of the particles.

Cationic Nanoemulsion

| Oily phase | |
|---|---|
| PEG 400 isostearate sold by Uniqema | 1% |
| Behenyltriammonium chloride | 1% |
| Avocado oil | 1% |

-continued

| | |
|---|---|
| Jojoba oil | 3% |
| Cyclopentamethylsiloxane | 2% |
| Aqueous phase | |
| Distilled water | 30% |
| Dipropylene glycol | 10% |
| Dilution phase | |
| Distilled water | qsp 100% |
| Preservative | 0.1% |

An emulsion is prepared by dispersing the oily phase in the aqueous phase under very vigorous agitation. The suspension obtained is then homogenized several times by means of a very high-pressure homogenizer, at a pressure of approximately 1200 b. The size of the particles is on the order of 50 nm, and the suspension is transparent. The dilution phase is then added.

As in the preceding cases, there is then added a suspension of siRNA (20 μM) in ratios ranging from 1:1 to 1:20 (siRNA: nanoemulsion). The siRNA will then become complexed on the surface of the particles.

EXAMPLE 2

Cell Targeting

Cell and tissue targeting was carried out in the reconstructed epidermis model developed by EPISKIN SNC. Two phases of growth kinetics of the model were chosen for topical application of the micelle/siRNA complex:

1 application on day 6 of growth of the epidermis, corresponding to an epidermis at the beginning of stratification and keratinization.

1 application on day 13 of growth of the epidermis, corresponding to a stratified and keratinized epidermis.

The siRNA chosen is Block-It Fluorescent Oligo (20 μM), such as described in the manual "Block-It Transfection Kit" (Catalog ref. No.: 13750-070, Invitrogen). It is a 25-nucleotide double stranded RNA coupled with fluorescein. The coded sequence has no homology with the human genome, and therefore makes it non-functional. This nucleotide was developed specifically for the study of cell targeting. When it is transfected, it is present in the cytoplasm and also penetrates into the cell nucleus.

Preparation of the Micelle/siRNA Complex:

3 μl of Block-It Fluorescent Oligo (20 μM), such as described in the manual "Block-It Transfection Kit" (Catalog ref. No.: 13750-070, Invitrogen), is mixed with 9 μl of cationic micelles E2 (octyl β-glucoside/cetyltriammonium bromide in the molar ratio of 5/1, 50 mM in distilled water).

Preparation of the Lipofectamine 2000/siRNA Mixture:

3 μl of Block-It Fluorescent Oligo (20 μM) is diluted in 50 μl of OptiMEM (Invitrogen) and mixed with 3 μl of Lipofectamine 2000 (Invitrogen) diluted in 12 μl of OptiMEM according to the supplier's protocol. The solution is incubated at ambient temperature for 20 minutes to permit complexing of the liposomes and of the siRNA.

Preparation of Control Solutions:

3 μl of Block-It Fluorescent Oligo (20 μM) is diluted in 9 μl of OptiMEM.

9 μl of cationic micelles E2 (octyl β-glucoside/cetyltriammonium bromide in the molar ratio of 5/1, 50 mM in distilled water) is diluted in 3 μl of OptiMEM.

The different mixtures and solutions are then deposited on different samples of EPISKIN epidermis and incubated under immersed conditions for 48 hours at 37° C. in the presence of 5% $CO_2$ in the differentiation medium supplied with the EPISKIN kit. The samples are then frozen in a mixture of dry ice and ethanol and cut into 5 μm sections by means of a cryostat (MICROM HM560). The sections are mounted in Vectrashield mounting medium (Vector Laboratories) containing 1.5 μg of DAPI and viewed under immunofluorescent conditions with filters appropriate for fluorescein and DAPI.

Figure 1C:
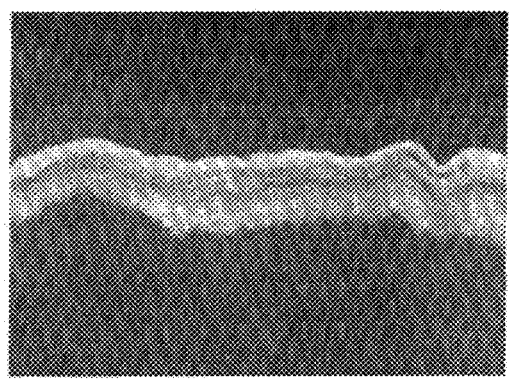
Figure 1D:
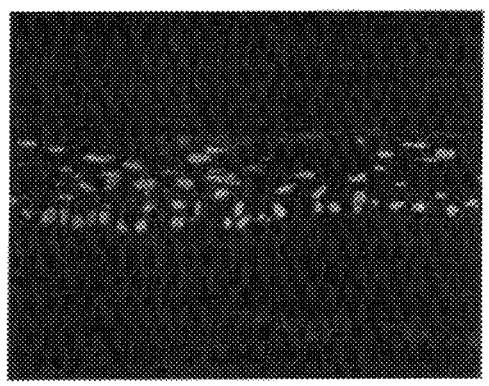
Figure 1E:
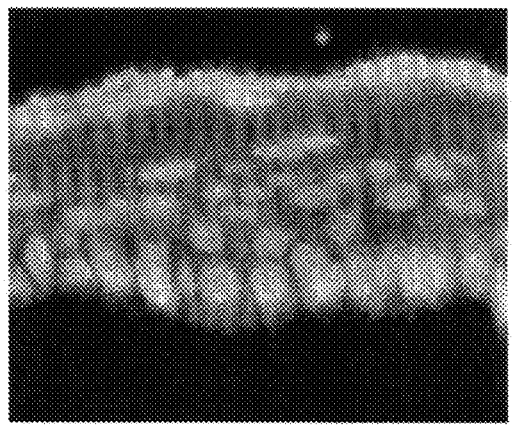
Figure 1F:
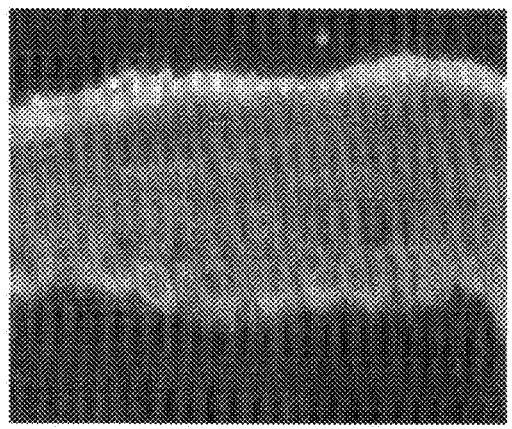

Observations:

Epidermis transfected on day 6: it is observed that, although the solution of Block-It Fluorescent Oligo (FIG. 1A) or the mixture of Lipofectamine 2000 (FIG. 1B) does not permit penetration of Block-It Fluorescent Oligo beyond the stratum corneum being formed, the mixture of E2 and Block-It Fluorescent Oligo permits penetration of the RNA duplex into the epidermis (FIGS. 1C, 1E, 1F). No non-specific marking is detected when E2 is applied alone (FIG. 1D). The surprising character of this observation is emphasized by the homogeneous presence of the Block-It Fluorescent Oligo in all cells of the epidermis, whereas it is known by the person skilled in the art that traditional transfection is efficient only in proliferating cells. In the reconstructed epidermis, only the basal cells proliferate, while the supra-basal cells become differentiated.

Figure 2A:
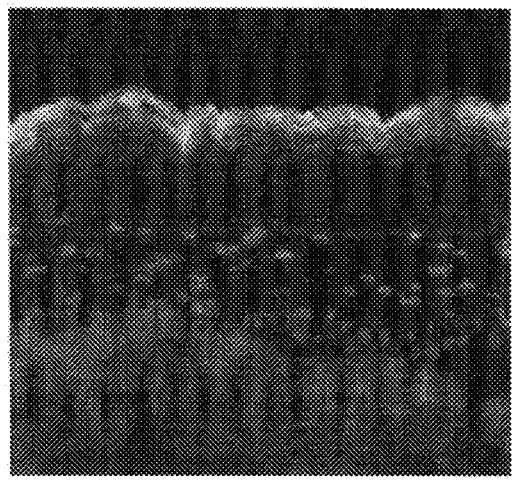

Epidermis transfected on day 13: as on day 6, the solution of Block-It Fluorescent Oligo alone does not penetrate the stratum corneum (FIG. 2A). The mixture of E2 and Block-It Fluorescent Oligo permits penetration of the fluorescent duplex into the different layers of the stratum corneum and into the different cells of the epidermis (FIGS. 2B and 2C), albeit with lower efficiency and homogeneity than on day 6.

EXAMPLE 3

Effect of a Formulation of Octyl Glucoside and CTAB in Different Concentrations on the Mortality of HaCaT Cells The effect of formula E2: 50 mM micelles of octyl glucoside/CTAB in 5/1 molar ratio is achieved by incubation for 4 days according to the following protocol on HaCaT cells (500 μl of medium seeded with 40,000 cells per well, B-It: Block-It Fluorescent Oligo (Invitrogen).

40,000 HaCaT cells per well are seeded in duplicate in a 24-well plate in 500 μl of complete DMEM+10% fetal calf serum.

1 μl of Block-It Fluorescent Oligo (Invitrogen) is diluted in 1 to 15 μl of micellar solution E2, composed of 50 mM of micelles of octyl glucoside and CTAB in 5/1 molar ratio and added to the culture medium, bringing the final concentration of micellar solution to 0.1 to 1.5 mM.

The cells are then incubated for 4 days at 37° C., the medium for one sample of the duplicates being changed on day 1, after which they are photographed.

The results obtained are presented in FIGS. 3A-3H and 4A-4D.

No difference is observed between the cells subjected to the same treatment with or without change of medium on day 1.

High mortality is observed for micellar solution concentrations below the CMC (approximately 1 mM), revealing the toxic effect of the vehicle in its free form, whereas good cell viability is observed above the CMC (1.5 mM).

The above written description of the invention provides a manner and process of making and using it such that any person skilled in this art is enabled to make and use the same, this enablement being provided in particular for the subject matter of the appended claims, which make up a part of the original description and including a kit comprising a skin model and a composition comprising at least one double stranded RNA oligonucleotide associated with at least one cationic particle of size smaller than or equal to 1 µm, of zeta potential between 10 and 80 mV, chosen from among surfactant micelles, block polymer micelles, liposomes of nonionic and cationic surfactants, niosomes, oleosomes, particles of nanoemulsions, nanocapsules, organic particles or inorganic particles; the use of a composition comprising at least one double stranded RNA oligonucleotide associated with at least one cationic particle of size smaller than or equal to 1 µm, of zeta potential between 10 and 80 mV, chosen from among surfactant micelles, block polymer micelles, liposomes of nonionic and cationic surfactants, niosomes, oleosomes, particles of nanoemulsions, nanocapsules, organic particles or inorganic particles for partial or total inhibition of protein expression by the cells of a skin model; and a method for preparation of a skin model, the said method comprising a step of administering, in the culture medium of the said model, a composition comprising at least one double stranded RNA oligonucleotide associated with at least one cationic particle of size smaller than or equal to 1 µm, of zeta potential between 10 and 80 mV, chosen from among surfactant micelles, block polymer micelles, liposomes of nonionic and cationic surfactants, niosomes, oleosomes, particles of nanoemulsions, nanocapsules, organic particles or inorganic particles.

Preferred embodiments of the invention similarly fully described and enabled include kits, characterized in that the cationic particle has a size smaller than or equal to 500 nm, characterized in that the cationic particle has a size smaller than or equal to 300 nm, characterized in that the cationic particle is a micelle of nonionic amphiphilic surfactants and cationic surfactants, characterized in that the block copolymer micelle is chosen from among a micelle of cationic amphiphilic block polymer, a micelle of nonionic amphiphilic block polymer and of cationic amphiphilic block polymer and a micelle of nonionic amphiphilic block polymer and of cationic surfactant.

Similarly enabled is a method for preparation of a skin model, characterized in that it comprises the supplementary step of application of an occlusive system, characterized in that it comprises the preliminary step of reducing the proportion of Ca2+ in the culture medium of the skin model, and characterized in that the permeability of the skin model is increased at the same time as the said composition is being applied As used above, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

As used herein, where a certain polymer is noted as being "obtained from" or "comprising", etc. one or more monomers (or monomer units) this description is of the finished polymer material itself and the repeating units therein that make up, in whole or part, this finished product. One of ordinary skill in the art understands that, speaking precisely, a polymer does not include individual, unreacted "monomers," but instead is made up of repeating units derived from reacted monomers.

The invention claimed is:

1. A kit comprising:
a skin model selected from a reconstructed in vitro skin model and an ex vivo skin model maintained in viable condition; and
a composition comprising at least one double stranded RNA oligonucleotide associated with at least one cationic surfactant micelle having a zeta potential of from 10 to 80 mV, wherein the micelle does not contain a block polymer and wherein the size of the cationic surfactant micelle is less than or equal to 500 nm.

2. The kit according to claim 1, wherein the size of the cationic surfactant micelle is less than or equal to 300 nm.

3. The kit according to claim 1, wherein the cationic surfactant micelle comprises a micelle of nonionic amphiphilic surfactants and cationic surfactants.

4. The kit according to claim 1, wherein the cationic surfactant micelle comprises surfactant(s) at a concentration of 0.1 to 10% by weight relative to the total weight of the composition.

5. The kit according to claim 1, wherein the cationic surfactant micelle comprises surfactant(s) at a concentration of 0.2 to 5% by weight relative to the total weight of the composition.

6. The kit according to claim 1, wherein the cationic surfactant micelle comprises at least one cationic surfactant selected from the group consisting of fatty amines, salts of fatty amines, and mixtures thereof.

7. The kit according to claim 1, wherein the cationic surfactant micelle comprises at least one cationic surfactant which is a quaternary ammonium salt.

8. The kit according to claim 6, wherein the quaternary ammonium salt is a tetraalkylammonium chloride or a tetraalkylammonium bromide.

9. The kit according to claim 7, wherein the quaternary ammonium salt is behenyltrimethylammonium chloride or behenyltrimethylammonium bromide.

10. A kit comprising:
a skin model selected from a reconstructed in vitro skin model and an ex vivo skin model maintained in viable condition; and
a composition comprising at least one double stranded RNA oligonucleotide associated with at least one surfactant micelle having a zeta potential of from 10 to 80 mV, wherein the micelle consists essentially of one or more cationic surfactants or consists essentially of at least one cationic surfactant and at least one nonionic amphiphilic surfactant and wherein the size of the cationic surfactant micelle is less than or equal to 500 nm.

11. The kit according to claim 10, wherein the micelle consists of one or more cationic surfactants or consists of at least one cationic surfactant and at least one nonionic amphiphilic surfactant.

12. A kit comprising:
a skin model selected from a reconstructed in vitro skin model and an ex vivo skin model maintained in viable condition; and
at least one double stranded RNA oligonucleotide associated with at least one surfactant micelle having a zeta potential of from 10 to 80 mV, wherein the micelle consists essentially of one or more cationic surfactants or consists essentially of at least one cationic surfactant and at least one nonionic amphiphilic surfactant and wherein the size of the cationic surfactant micelle is less than or equal to 500 nm.

13. The kit according to claim 12, wherein the micelle consists of one or more cationic surfactants or consists of at least one cationic surfactant and at least one nonionic amphiphilic surfactant.

14. The kit according to claim 1, wherein the cationic surfactant micelle comprises at least one cationic surfactant selected from the group consisting of fatty amines, salts of fatty amines, and mixtures thereof.

15. The kit according to claim 1, wherein the cationic surfactant micelle comprises at least one cationic surfactant which is a quaternary ammonium salt.

16. The kit according to claim 14, wherein the quaternary ammonium salt is a tetraalkylammonium chloride or a tetraalkylammonium bromide.

17. The kit according to claim 15, wherein the quaternary ammonium salt is behenyltrimethylammonium chloride or behenyltrimethylammonium bromide.

18. The kit according to claim 3, wherein the nonionic amphiphilic surfactant is selected from the group consisting of C6-C30 esters or ethers of POP, POE, glycerol, polyglycerol, sorbitan, sucrose, glucose, maltose, and mixtures thereof.

19. The kit according to claim 11, wherein the micelle consists of one or more one cationic surfactants.

20. The kit according to claim 11, wherein the micelle consists of at least one cationic surfactant and at least one nonionic amphiphilic surfactant.

* * * * *